United States Patent [19]
Bonner et al.

[11] Patent Number: 5,968,086
[45] Date of Patent: Oct. 19, 1999

[54] PACING AND CARDIOVERSION LEAD SYSTEMS WITH SHARED LEAD CONDUCTORS

[75] Inventors: Matthew D. Bonner, Plymouth; Adrianus P. Donders, Andover, both of Minn.

[73] Assignee: Medtronic, Inc., Minneapolis, Minn.

[21] Appl. No.: 09/028,143

[22] Filed: Feb. 23, 1998

[51] Int. Cl.$^6$ ............................................. A61N 1/05
[52] U.S. Cl. .................................................. 607/122
[58] Field of Search .............................. 607/116, 119, 607/122; 600/373, 374

[56] References Cited

U.S. PATENT DOCUMENTS

| | | |
|---|---|---|
| 4,440,172 | 4/1984 | Langer . |
| 4,499,907 | 2/1985 | Kallok et al. ............................ 607/122 |
| 4,595,009 | 6/1986 | Leinders . |
| 4,614,192 | 9/1986 | Imran et al. . |
| 4,791,935 | 12/1988 | Baudino et al. . |
| 4,999,907 | 3/1991 | Pawlenko . |
| 5,014,696 | 5/1991 | Mehra . |
| 5,044,375 | 9/1991 | Bach, Jr. et al. . |
| 5,325,870 | 7/1994 | Kroll et al. ............................. 607/122 |
| 5,336,253 | 8/1994 | Gordon et al. . |
| 5,628,776 | 5/1997 | Paul et al. ............................. 607/119 |

*Primary Examiner*—William E. Kamm
*Assistant Examiner*—George R. Evanisko
*Attorney, Agent, or Firm*—Reed A. Duthler; Harold R. Patton

[57] ABSTRACT

An implantable electrical lead having an elongated insulative lead body carrying a cardioversion/defibrillation electrode and a sensing electrode spaced from the cardioversion/defibrillation electrode. A diode enclosure is mounted in the lead body between the cardioversion/defibrillation electrode and the sensing electrode, the diode enclosure having conductive end walls and including a diode or diodes therein coupled between the conductive end walls. The enclosure is also provided with a feedthrough tube extending through said enclosure, passing through the end walls. An elongated conductor extends through the lead body and through the feedthrough tube of said enclosure and is electrically coupled to the sensing electrode. The cardioversion/defibrillation electrode and the sensing electrode are each electrically coupled to one of the conductive end walls of the diode enclosure.

15 Claims, 4 Drawing Sheets

PACING AND CARDIOVERSION LEAD SYSTEMS WITH SHARED LEAD CONDUCTORS

BACKGROUND OF THE INVENTION

This invention relates to electrode leads for use in the detection and control of cardiac bradyarrhythmias and tachyarrhythmias, and particularly to a lead including cardioversion/defibrillation electrodes and pacing/sensing electrodes on a common lead body.

Research to provide an automatic implantable pacemaker/cardioverter/defibrillator has been in progress for over twenty years and has led to the implantation in recent years of several versions of such systems. Over the same period of time, considerable research and development effort has been expended in the development of cardioversion and defibrillation leads. In this context, both unipolar and bipolar pacing and sensing have been employed. Recently, it has also been disclosed that biphasic cardioversion and defibrillation pulses provide substantial benefits.

The traditional approaches to adding pacing and sensing electrodes to cardioversion/defibrillation leads require a separate conductor for each pacing and sensing electrode and for each independently usable defibrillation electrode. Thus, bipolar sensing typically requires at least three conductors, and in the case of multiple cardioversion/defibrillation electrodes, four or more conductors. In embodiments employing multiple cardioversion/defibrillation electrodes, even unipolar sensing correspondingly typically requires at least three conductors. As the size and complexity of these leads increases with each additional conductor, a reduction of the number of conductors per lead is desirable.

In endocardial leads, a further complication arises. It is believed desirable in many cases to locate a right ventricular cardioversion/defibrillation electrode as close to the apex of the heart as possible. However, placement of one or two sense/pace electrodes at the distal end of the lead (a preferred location) typically results in location of the defibrillation electrode in a less apical location, in order to provide space for the pace/sense electrode or electrodes.

Bipolar sensing has been disclosed to be particularly effective in the detection of "near field" ECGs which are used for arrhythmia detection and or synchronization of delivered cardioversion and defibrillation shocks in some current devices. While workable, it is believed less than optimal to employ a small surface area pace/sense electrode in conjunction with a large surface area cardioversion/defibrillation electrode for sensing the near field ECG. The large surface area cardioversion electrode may extend over or near enough to conduction pathways which reflect both atrial and ventricular originated ECG components. If large enough, the "far field" components can in some cases be detected and confuse the tachyarrhythmia detection circuitry and algorithm of the pulse generator. Consequently, a number of references recommend the use of a separate pair of closely spaced, small surface area pace/sense electrodes for sensing. For example, see U.S. Pat. No. 4,614.192, issued to Imran et al., and U.S. Pat. No. 5,044,375, issued to Bach, et al. It should also be Noted that Implantable pacemaker/cardioverter/defibrillators currently in clinical testing, manufactured by Medtronic, Inc., employ ventricular endocardial leads as generally illustrated in U.S. Pat. No. 5,014,696, issued to Mehra, which include a bipolar electrode pair for sensing, located adjacent the distal end of the lead, and a large surface area coil electrode located proximal to the bipolar pair.

U.S. Pat. No. 4,440,172 describes a number of embodiments of pacing and cardioversion electrodes and leads which provide for unipolar pacing and sensing through the use of endocardial ventricular tip electrodes or an epicardial button electrodes paired with epicardial defibrillation electrodes. In one embodiment, a combined defibrillator-pacer system is depicted where the monophasic defibrillation shocks and pacing pulses are transmitted over the same conductor pair through the lead body but are routed to different electrodes on the basis of their polarity using steering diodes located within the lead. However, this approach would appear to be problematic in the event that biphasic cardioversion/defibrillation pulses were to be employed.

In U.S. Pat. No. 4,999,907, a transvenous, endocardial version lead is described which employs a pair of distal electrodes and a pair of proximal electrodes, which are respectively intended to be lodged in the ventricular apex of the right ventricular chamber of the heart and the superior vena cava. Each pair of electrodes is intended to be electrically connected in common by circuitry within the implantable cardioverter during cardioversion. However during sensing and pacing, the closely spaced distal ventricular electrodes are connected to an ECG sense amplifier and a pacing energy pulse generator. The lead also includes circuitry for limiting the voltage of shocks delivered by the lead. U.S. Pat. No. 4,595,009 discloses switching circuitry which controls the interconnection of the pulse generators, sense amp and electrodes during pacing, sensing and cardioversion in conjunction with a lead generally as illustrated in the '907 patent, but lacking the voltage limiting circuitry.

One additional proposed approach to reducing the numbers of lead conductors in cardioversion and defibrillation leads has been to allow a sensing or pacing electrode to share a conductor with a cardioversion or defibrillation electrode by inserting back-to-back zener diodes between the sensing or pacing electrode and the cardioversion or defibrillation electrode. Examples of such leads may be found in U.S. Pat. No. 5,336,253, issued to Mehra et al. and incorporated herein by reference in its entirety.

SUMMARY OF THE INVENTION

For purposes of this application, "cardioversion" is used hereafter in a broad sense, as including the application of relatively high energy and high voltage shocks to the heart to terminate tachyarrhythmias including fibrillation and malignant tachycardias. Similarly, "pacing" is used in a broad sense as including the application of relatively low energy and low voltage pacing impulses to maintain an adequate heart rate or to break a tachycardia by stimulating the patient's heart.

It is an object of the present invention to reduce the total number of lead conductors for connection to a pacing and cardioversion lead which includes an electrode or electrodes for sensing and pacing the heart in addition to one or more large surface area cardioversion electrodes.

In the context of endocardial ventricular leads, it is an object of the present invention to provide an electrode or electrode pair for sensing adjacent the ventricular apex while still providing a cardioversion electrode which also is located as close to the ventricular apex as possible.

These and other objects of the present invention are realized by providing leads having at least one small surface area pacing or sensing electrode closely spaced to a large surface area cardioversion/defibrillation electrode with a conductor extending to said pacing or sensing electrode through the lead body and by incorporating one or more diodes particularly optimized for incorporation in the body of an implantable lead. The diode or diodes connect the large surface area cardioversion electrode and the smaller surface area pace/sense electrode during delivery of cardioversion pulses, and functionally disconnects the large surface electrode from the pacing or sensing electrode during sensing.

In a first preferred embodiment, back to back zener diodes are included as in the above cited Mehra et al patent. In a second preferred embodiment, two diodes connected in parallel at opposite polarities are connected between the cardioversion or defibrillation electrode and the pacing or sensing electrode. In both of these preferred embodiments, the diodes are enclosed in a hermetic housing optimized for inclusion in a medical lead.

The housing is configured to have an outer circumferential wall which may in preferred embodiments correspond generally to the configuration of the outer surface of the lead body in its intended location. The enclosure also has proximal and distal end walls which extend across all or a substantial portion of the cross section of the lead body. The proximal and distal walls are fabricated of a conductive material and serve to allow connection to the diodes located with the enclosure. The circumferential wall is preferably non-conductive, so that the diodes within the enclosure provide the only electrical connection between the proximal and distal walls. One or more non-conductive feedthrough tubes extend between the proximal and distal end walls, allowing passage of one or more conductors through the enclosure.

BRIEF DESCRIPTION OF THE DRAWINGS

The above and other object and advantages of the present invention will be more clearly understood by reference to the following description, the appended claims and their accompanying drawings, in which like reference numerals designate like parts throughout the figures thereof and wherein:

DETAILED DESCRIPTION OF THE PREFERRED EMBODIMENTS

Figure 1:
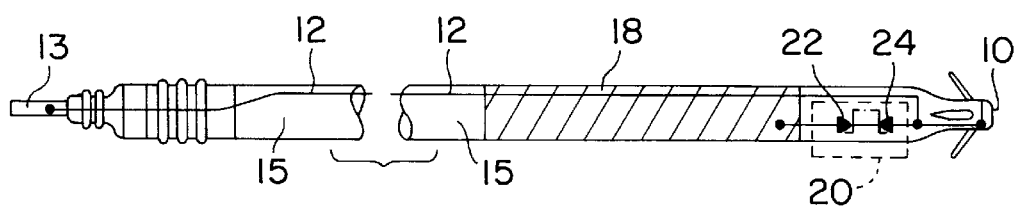
FIG. 1 is a schematic illustration of a first, endocardial, unipolar lead embodiment of the invention.
Figure 2:
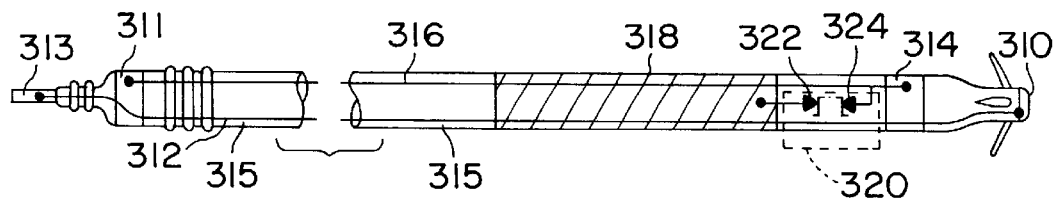
FIG. 2 is a schematic illustration of a second, endocardial, unipolar lead embodiment of the invention.
Figure 3:
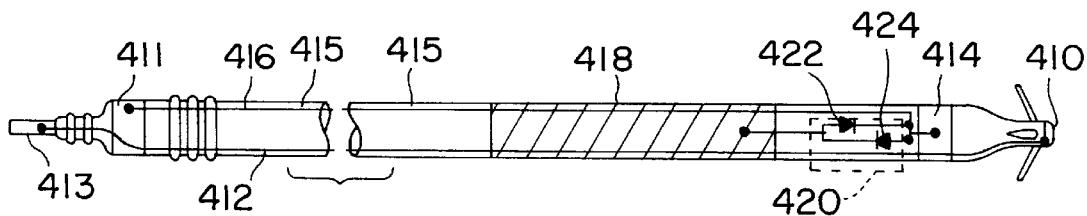
FIG. 3 is a schematic illustration of a third, endocardial, bipolar lead embodiment of the invention.

FIGS. 1–3 are schematic representations of the electrical interconnection of at least one cardioversion/defibrillation electrode and a pace/sense electrode to a single conductor and connector and employing diodes within the lead which effectively isolate the cardioversion/defibrillation electrode from the pace/sense electrode during sensing. The diodes respond to the magnitude of the applied cardioversion shock to direct the shock to the cardioversion/defibrillation electrode commonly with the at least one pace/sense electrode.

FIG. 1 illustrates a first, unipolar embodiment of the present invention, schematically illustrating the arrangement of tip electrode 10 and elongated cardioversion electrode 18. In this embodiment, the tip electrode 10 is coupled to the elongated cardioversion electrode 18 through switching circuit 20 which may take the form of back-to-back zener diodes 22, 24.

In the embodiment of FIG. 1, sensing and pacing may take place between the housing of the implantable pacemaker/cardioverter/defibrillator to which the lead is attached and tip electrode 10. Tip electrode 10 is mounted at the distal end of insulative lead body 15 and is coupled to conductor 12, which in turn is coupled to connector 13. Since pacing pulses and ECG signal voltage amplitudes fall far below the breakdown voltages of diodes 22, 24, ECG signal contribution from the more proximal end of the elongated cardioversion electrode 18 which may extend 10 or more centimeters along the lead body is not added to the signals picked up by electrode pair 10. When cardioversion shocks are delivered, on the other hand, the terminal 13 is coupled to one of the output terminals of the cardioversion pulse generator, and the tip electrode 10 and the elongated cardioversion electrode 18 are electrically connected together as a single effective electrode by operation of the back-to-back zener diodes 22, 24 which may be selected to break down at three to ten volts on the leading edge of the cardioversion shock.

It will be understood that a second cardioversion electrode or electrode may be also optionally be located on the lead of FIG. 1, for example placed such that it is located in the superior vena cava after implant. However, more typically a second cardioversion electrode and optionally third or fourth cardioversion electrodes will be located on separate leads or on the housing of an associated pacemaker/cardioverter/defibrillator.

FIG. 2 illustrates a second embodiment of the present invention, schematically illustrating the arrangement of tip electrode 310, distal ring electrode 314 and elongated cardioversion electrode 318. In this embodiment, the ring electrode 314 is coupled to the elongated cardioversion electrode 318 through switching circuit 320 which may take the form of back-to-back zener diodes 322, 324, in a manner analogous to the interconnection of the tip and cardioversion electrodes as illustrated in FIG. 1. Ring electrode 314 is coupled to connector 311 through conductor 316. Tip electrode 310, which is mounted at the distal end of insulative lead body 315, is coupled to connector 313 through conductor 312.

In the embodiment of FIG. 2, bipolar sensing and pacing may take place between the 0.5 to 3.0 centimeter spaced tip electrode 310 and ring electrode 314 through conductors 312 and 316, respectively. Since pacing pulses and ECG signal voltage amplitudes fall far below the breakdown voltages of diodes 322, 324, ECG signal contribution from the more proximal end of the elongated cardioversion electrode 318 which may extend 10 or more centimeters along the lead body is not added to the signals picked up across the bipolar sensing electrode pair 310, 314. When cardioversion shocks are delivered, the terminal 313 is coupled to one of the output terminals of the cardioversion pulse generator, and both the ring electrode 314 and the elongated cardioversion electrode 318 are electrically connected together as a single effective electrode by operation of the back-to-back zener diodes 322, 324.

It will be understood that a second cardioversion electrode or electrode may be also be located on the lead of FIG. 2.

However, more typically a second cardioversion electrode and optionally third or fourth cardioversion electrodes will be located on separate leads or on the housing of an associated pacemaker/cardioverter/defibrillator.

The embodiments of FIG. 2, and of FIG. 3, as discussed below, are particularly advantageous in eliminating the far-field signal contribution to bipolar sensing which would occur if the cardioversion electrode 318 were paired with tip electrode 310 for sensing, while retaining an apical location for the effective distal end of the cardioversion electrode. In addition, the embodiments of FIGS. 3 and 4 accomplish these desirable results using only two conductors in the lead body.

FIG. 3 illustrates a third embodiment of the present invention, corresponding generally to the embodiment illustrated in FIG. 2, but substituting a pair of diodes 422, 424 connected in parallel but at opposite polarities between ring electrode 414 and cardioversion/defibrillation electrode 418 for the back-to-back zener diodes 322, 324, in FIG. 2. Because the amplitude of sensed intrinsic depolarization signals is less than the diode drop of diodes 422 and 424, the cardioversion/defibrillation electrode 418 is effectively uncoupled from the ring electrode 414 during sensing. Tip electrode 410, which is mounted at the distal end of insulative lead body 315, is coupled to connector 413 through conductor 412.

Figure 4:
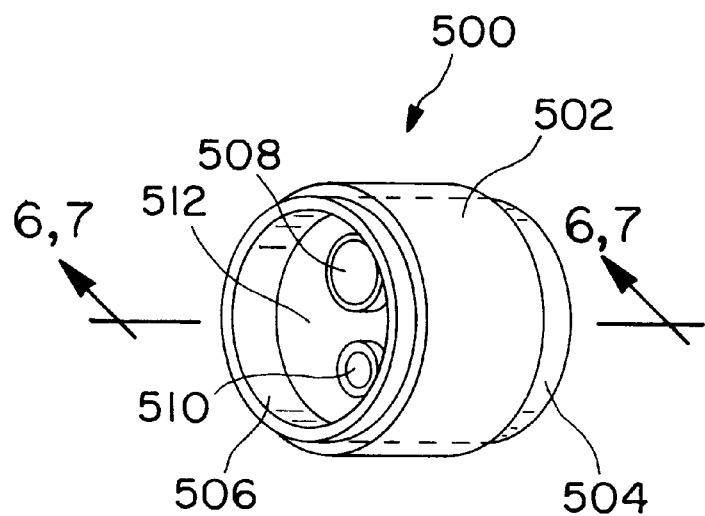
FIG. 4 is a perspective drawing of a diode enclosure according to the present invention.

FIG. 4 is a perspective view of a diode enclosure 500 of the type appropriate for inclusion in the leads illustrated in FIGS. 1–3, discussed above. The enclosure includes an outer circumferential portion 502 which may be formed of a sapphire tube and two end portions 504 and 506, each of which take the form of a shallow metallic cup-shaped member inserted into and braised to the circumferential member 502. For example, end members 504 and 506 may be fabricated of titanium or stainless steel and brazed to a sapphire outer member 502 using a gold based braze, as discussed in U.S. Pat. No. 4,791,935 issued to Baudino et al. and incorporated herein by reference in its entirety.

Each of the end members 504 and 506 includes a wall portion, visible in conjunction with end member 506 at 512. These wall portions define the proximal and distal end walls of the enclosure. Extending through the proximal and distal end walls are two ceramic feedthrough tubes 508 and 510 which serve to allow passage of conductors through the diode enclosure 500. In the embodiment illustrated in FIG. 4, it is anticipated that the diode enclosure will be used in conjunction with leads as illustrated in FIGS. 2 and 3 which include a tip electrode, a ring electrode and a cardioversion electrode. The larger ceramic feedthrough tube 508 allows for passage of a coiled conductor therethrough, typically coupled to the distal or tip electrode of the lead, as illustrated at 310 and 410 in FIGS. 2 and 3 respectively. The smaller feedthrough tube 510 allows for passage of a smaller diameter conductor which is coupled to the ring electrode, corresponding to electrodes 314 and 414 in FIGS. 2 and 3 respectively, which are located distal to the enclosure 500. The conductive end members 504 and 506 are electrically coupled to the diodes within the enclosure 500 and may be used to couple the diodes therein to conductors or electrodes in the lead. The configuration of the end members 504 and 506 may be varied from that illustrated in order to facilitate welding, swaging, crimping, or other mechanisms for interconnecting the end members to leads and/or electrodes in the lead.

Figure 5:
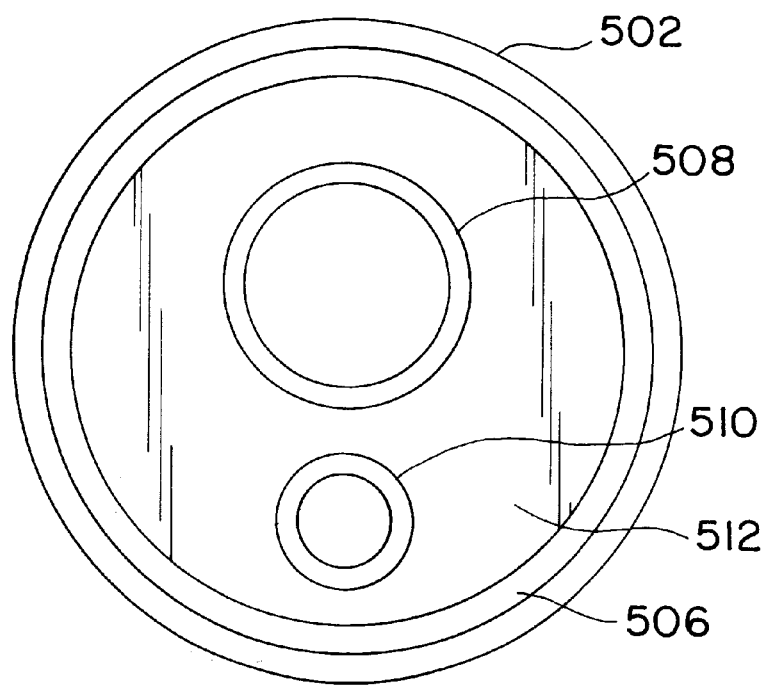
FIG. 5 is a plan view of the proximal end of a diode enclosure according to the present invention.

FIG. 5 illustrates a plan view of the proximal end of the enclosure illustrated in FIG. 4. The end member 506 is shown inserted in and brazed to the tubular sapphire outer member 502. Ceramic feedthrough tubes 508 and 510 extend entirely through the enclosure and are brazed or otherwise sealed to the end wall 512 of the end member 506 and to the corresponding wall portion of end member 504 (FIG. 4) to provide a hermetic enclosure for the diodes therein.

Figure 6:
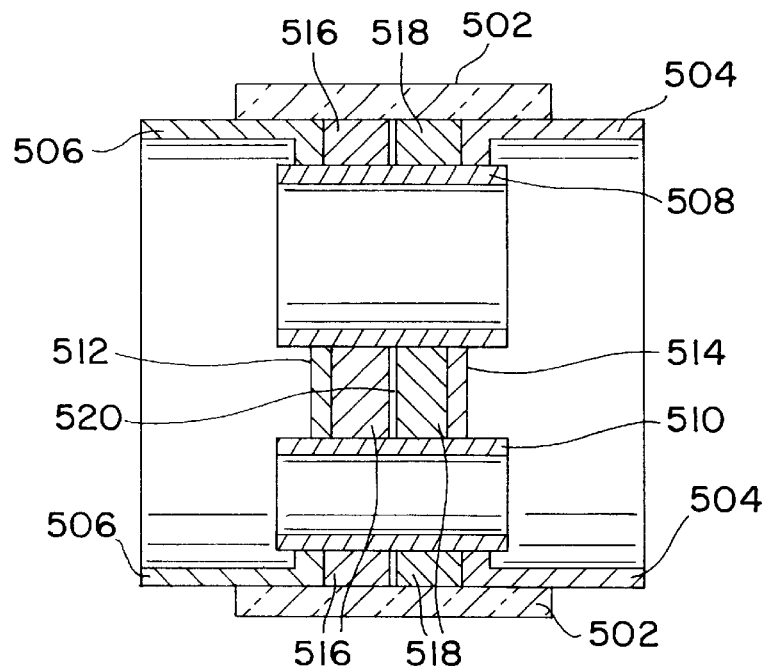
FIGS. 6 and 7 are sectional views through the diode enclosure of FIGS. 4 and 5.

FIG. 6 illustrates a cross-sectional view through a first embodiment of a diode enclosure corresponding to that illustrated in FIGS. 4 and 5. Cup-shaped end members 504 and 506 are visible in cross-section, with cylindrical ceramic feedthrough tubes 508 and 510 extending through the enclosures, and through the end wall portions 512 and 514 of end members 506 and 504. Visible within the enclosure are zener diodes 516 and 518 which are coupled face to face or back to back within the enclosure. Diode 516 is electrically coupled to the end wall portion 512 of end member 506, by means of conductive epoxy or otherwise, and is in turn coupled to diode 518 by means of an internal conductive layer 520. Diode 518 is similarly coupled to wall portion 514 of end member 504. When incorporated into a lead, end member 506 will be coupled to a cardioversion or defibrillation electrode by welding or otherwise while end member 504 will be coupled to a ring electrode, as discussed above. One conductor extending from the proximal end of the lead body will pass through feedthrough 510 to be coupled to the ring electrode. A second conductor, typically a coiled conductor, will pass from the proximal end of the lead through feedthrough 508 to the tip electrode.

While the diode enclosure illustrated in FIG. 6, as discussed above, is particularly optimized for use in conjunction with leads having three electrodes as disclosed in FIGS. 2 and 3, it may readily be modified for use in a lead having only two electrodes as illustrated in FIG. 1. In such case, feedthrough tube 510 will simply be dispensed with, end member 504 will be coupled to the tip electrode, which in turn would be coupled to the conductor, typically a coiled conductor, extending through feedthrough tube 508.

Figure 7:
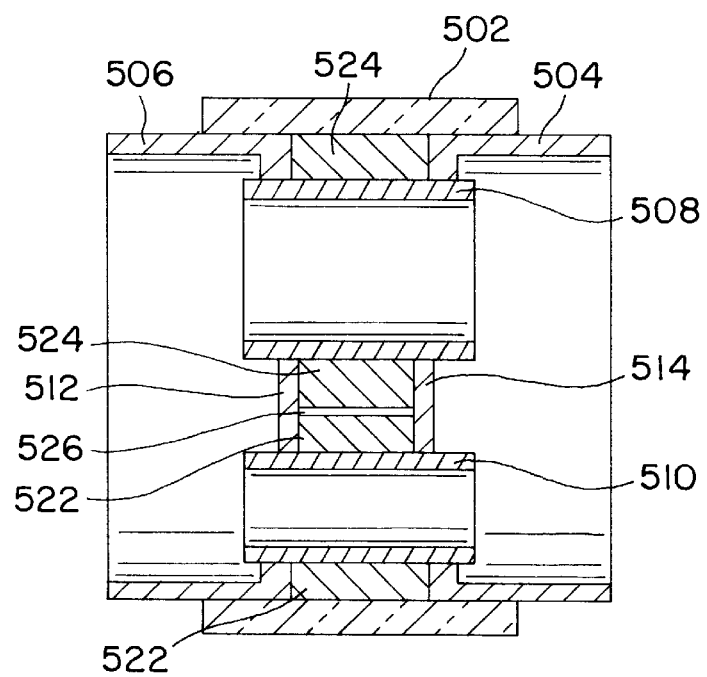

FIG. 7 is a plan view of an alternative embodiment of an enclosure as illustrated in FIGS. 5 and 6. All elements correspond precisely to identically labeled elements in FIG. 6. This enclosure differs from that in FIG. 6 in that it includes two conventional diodes 522 and 524 extending between and coupled to the wall portions 512 and 514 of end members 506 and 504, respectively. The two diodes are separated from one another by an insulative layer 526, producing the arrangement illustrated schematically in FIG. 3. The diode enclosure of FIG. 7 is interconnected to cardioversion/defibrillation and pace/sense electrodes in precisely the same fashion as that illustrated in FIG. 6.

Figure 8:
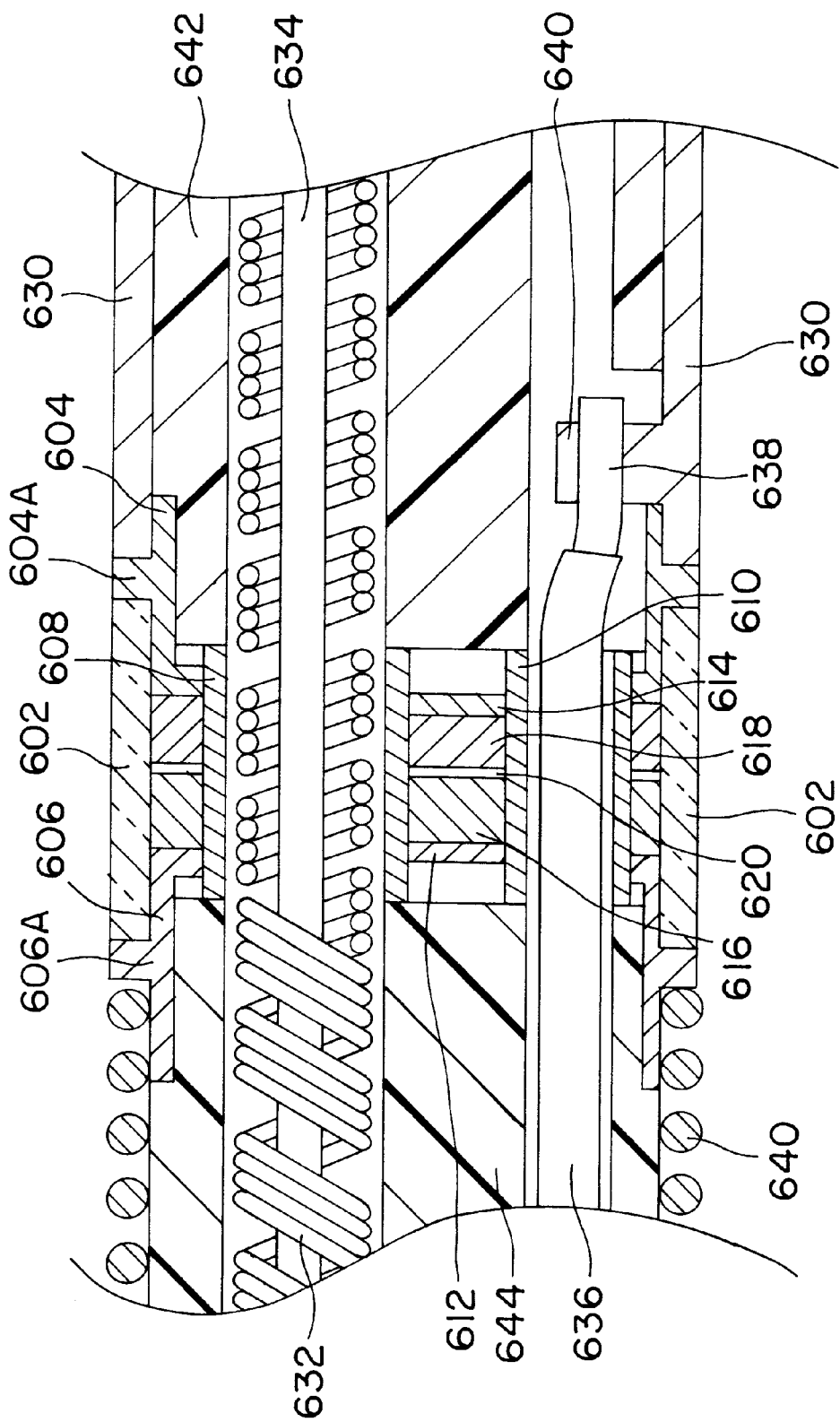
FIG. 8 is a sectional view through a lead according to the present invention, including a diode enclosure according to the present invention.

FIG. 8 illustrates a cross-section through a lead employing an enclosure according to the present invention. This enclosure corresponds generally to that illustrated in FIG. 6, with slight modifications to facilitate coupling the enclosure to a ring electrode 630 and a cardioversion/defibrillation electrode 640. Cup-shaped conductive end members 606 and 604 are inserted into non-conductive, circumferential member 602 and brazed thereto as discussed above. End members 604 and 606 are provided with circumferential flanges 604A and 606A facilitating welding of the end members to ring electrode 630 and to coiled cardioversion/defibrillation electrode 640. Feedthrough tubes 608 and 610, diodes 616, 618 and conductive layer 620 correspond to feedthrough tubes 508 and 510, diodes 516 and 518 and conductive layer 520 as illustrated in FIG. 6. Diodes 616 and 618 are coupled back to back between the conductive end wall portions 612 and 614 of end members 604 and 608.

The enclosure is shown mounted within a lead generally corresponding to that illustrated to that of FIG. 2 above, with ring electrode 630 coupled to a first insulative conductor 636 which passes through feedthrough tube 610, and has its uninsulated portion 638 inserted into an aperture through boss 640 which is then compressed or staked to retain the conductor in contact with ring electrode 630. A coiled conductor 632 passes through feedthrough tube 608, and extends to the tip electrode of the lead, corresponding to electrode 310 in FIG. 2. A stylet 634 is shown extending through the internal lumen of coiled conductor 632. Proximal and distal to the enclosures are located insulative lead body portions 642 and 644, carrying internal lumens corresponding in configuration generally to the interior dimensions of feedthrough tubes 608 and 610. Distal lead body portion 642 is inserted into the assembly comprising the enclosure and ring electrode 630 and is maintained therein by means of adhesive, backfill, or other conventional mechanism. Proximal lead body portion 644 is inserted into end member 604 and maintained therein by means of adhesive, backfill, or other conventional mechanism. Cardioversion/defibrillation coil 640 is welded to end member 604, adjacent circumferential flange 606A. Ring electrode 604 is likewise welded to end member 604 at circumferential flange 604A.

The embodiment of FIG. 8 illustrates only one of any number of possible configurations in which a diode enclosure according to the present invention may be employed. The enclosure is believed adaptable to lead configurations, including those in which the ring electrode and cardioversion/defibrillation electrode are separated from one another along the lead body, in which case the conductive end members 604 and 606 might be interconnected in substantially different fashion to the cardioversion and ring electrodes. For example, short lengths of flexible conductors may interconnect the enclosure with the cardioversion/defibrillation electrodes located on the lead body.

It should likewise be understood that in the context of the present invention, the leads employing a diode enclosure according to the present invention may include additional electrodes, sensors, and/or other components. Similarly, in conjunction with the pace/sense electrode and defibrillation electrodes to be employed in conjunction with the lead, various electrode configurations may be employed. Any conventionally known pace/sense electrode construction and any conventionally known cardioversion/defibrillation electrode construction may be substituted for those illustrated in the present case, which are intended to be purely exemplary.

Other modifications of the embodiments of the pacing and cardioversion electrode systems of the present invention will become readily apparent to those skilled in the argument in light of the foregoing disclosure, which should be considered exemplary, rather than limiting with regard to the scope of the claims that follow.

What is claimed is:

1. An implantable electrical lead comprising:
   an elongated insulative lead body;
   a cardioversion/defibrillation electrode, mounted to said lead body;
   a sensing electrode, mounted along said lead body, spaced from said cardioversion/defibrillation electrode;
   a diode enclosure mounted in said lead body between said cardioversion/defibrillation electrode and said sensing electrode, said diode enclosure comprising a hermetic enclosure having conductive end walls and including a first diode therein coupled between said conductive end walls, said enclosure also provided with a feedthrough tube extending through said enclosure, passing through said end walls; and
   an elongated conductor extending through said lead body and through said feedthrough tube of said hermetic enclosure and electrically coupled to said sensing electrode; and
   wherein said cardioversion/defibrillation electrode and said sensing electrode are each electrically coupled to one of said conductive end walls of said hermetic enclosure.

2. A lead according to claim 1 wherein said hermetic enclosure further comprises a second diode mounted therein coupled between said conductive end walls.

3. A lead according to claim 2 wherein said first and second diodes are coupled in parallel at opposite polarities.

4. A lead according to claim 2 wherein said first and second diodes are coupled in series at opposite polarities.

5. A lead according to claim 1 or claim 2 or claim 3 or claim 4 wherein said hermetic enclosure comprises a second feedthrough tube and wherein said lead body comprises a second elongated conductor which passes through said feedthrough tube.

6. An implantable electrical lead comprising:
   an elongated insulative lead body;
   first and second elongated conductors extending within said lead body;
   a cardioversion/defibrillation electrode, mounted to said lead body;
   a sensing electrode, mounted to said lead body and coupled to the first elongated conductor;
   a hermetic diode enclosure having first and second ends and mounted in said lead body, said diode enclosure comprising a hermetic enclosure including a first diode therein coupled between said first elongated conductor and said cardioversion/defibrillation electrode, said hermetic enclosure further comprising a feedthrough tube extending through said first and second ends of said enclosure, said second elongated conductor passing through said feedthrough tube.

7. A lead according to claim 6 wherein said enclosure further comprises a second feedthrough tube and wherein said first elongated conductor passes through said second feedthrough tube.

8. A lead according to claim 6 or claim 7 wherein said hermetic enclosure further comprises a second diode mounted therein coupled between said, first elongated conductor and said cardioversion/defibrillation electrode.

9. A lead according to claim 8 wherein said first and second diodes are coupled in parallel at opposite polarities.

10. A lead according to claim 8 wherein said first and second diodes are coupled in series at opposite polarities.

11. A lead according to claim 8, further comprising an additional electrode coupled to said second conductor.

12. An implantable electrical lead comprising:
   an elongated insulative lead body;
   a first elongated conductor extending within said lead body;
   a cardioversion/defibrillation electrode, mounted to said lead body;
   a sensing electrode, mounted to said lead body and coupled to the first elongated conductor;
   a hermetic diode enclosure having first and second ends and mounted in said lead body, said diode enclosure comprising a hermetic enclosure including a diode therein coupled between said first elongated conductor and said cardioversion/defibrillation electrode, said hermetic enclosure further comprising a feedthrough tube extending through said first and second ends of said enclosure, said first elongated conductor passing through said feedthrough tube.

13. A lead according to claim 12 wherein said hermetic enclosure further comprises a second diode mounted therein coupled between said, first elongated conductor and said cardioversion/defibrillation electrode.

14. A lead according to claim 13 wherein said first and second diodes are coupled in parallel at opposite polarities.

15. A lead according to claim 13 wherein said first and second diodes are coupled in series at opposite polarities.

* * * * *